United States Patent [19]

Bock et al.

[11] Patent Number: 4,866,752

[45] Date of Patent: Sep. 12, 1989

[54] X-RAY EXAMINATION APPARATUS COMPRISING A PILLAR CARRYING AN X-RAY SYSTEM

[75] Inventors: Hans-Christian Bock; Karlheinz Kaul, both of Uëttenreuth, Fed. Rep. of Germany

[73] Assignee: Siemens Aktiengesellschaft, Berlin and Munich, Fed. Rep. of Germany

[21] Appl. No.: 256,264

[22] Filed: Oct. 13, 1988

Related U.S. Application Data

[63] Continuation of Ser. No. 164, Jan. 2, 1987, abandoned.

[30] Foreign Application Priority Data

May 12, 1986 [DE] Fed. Rep. of Germany ... 8612867[U]

[51] Int. Cl.[4] .............................................. H05G 1/02
[52] U.S. Cl. .................................. 378/197; 378/193; 378/198
[58] Field of Search ................ 378/189, 193, 195–198; 248/125

[56] References Cited

U.S. PATENT DOCUMENTS

| | | | |
|---|---|---|---|
| 2,513,915 | 7/1950 | Caldwell | 378/193 |
| 2,822,477 | 2/1958 | Kizaur | 378/179 |
| 2,835,520 | 5/1958 | Schiring et al. | 403/63 |
| 3,609,355 | 9/1971 | Schwarzer | 378/195 |
| 3,833,813 | 9/1974 | James | 378/196 |
| 3,862,734 | 1/1975 | Buchin et al. | 248/125 |
| 4,329,587 | 3/1982 | Nieminen | 378/196 |
| 4,358,856 | 11/1982 | Stivender et al. | 378/197 |
| 4,481,656 | 11/1984 | Janssen et al. | 378/196 |
| 4,653,083 | 3/1987 | Rossi | 378/197 |

FOREIGN PATENT DOCUMENTS

1020382 2/1953 France .

OTHER PUBLICATIONS

Product Brochure "Angioskip C" of Siemens-Elema AB.

Primary Examiner—Carolyn E. Fields
Assistant Examiner—David P. Porta
Attorney, Agent, or Firm—Hill, Van Santen, Steadman & Simpson

[57] ABSTRACT

The invention relates to an X-ray examination apparatus comprising a vertical pillar at which a truck carrying an X-ray system is longitudinally displaceable. The pillar is a closed box profile and includes a U-shaped depression proceeding in longitudinal direction at each of two parallel long sides lying opposite one another, whereby the depressions serve as rails for the truck longitudinally displaceable on the pillar.

4 Claims, 2 Drawing Sheets and # 4,866,752

X-RAY EXAMINATION APPARATUS COMPRISING A PILLAR CARRYING AN X-RAY SYSTEM

This is a continuation of application Ser. No. 000,164 filed Jan. 2, 1987, now abandoned.

BACKGROUND OF THE INVENTION

1. Field of the Invention

The invention relates to an x-ray examination apparatus comprising a pillar carrying an x-ray system, this pillar being displaceable in parallel rails at the floor and at the ceiling of the examination room.

2. Description of the Prior Art

Given an x-ray examination apparatus of the type described above, a C-bend having an x-radiator and a radiation receiver at its ends can be provided as x-ray system. An apparatus of this type can be employed for angiocardiography and for interventional techniques. The area of the patient to be examiner is thereby selected by adjusting the C-bend along its circumferential direction, by pivoting the C-bend and by displacement of the pillar.

SUMMARY OF THE INVENTION

An object of the invention is to provide an x-ray examination apparatus of the type described above such that the x-ray system is longitudinally displaceable on the pillar in a simple way.

This object is achieved in accord with the invention in that the pillar has a closed box profile and includes U-shaped depressions proceeding in longitudinal direction lying opposite one another at each of two parallel long sides, whereby the depressions serve as rails for a truck longitudinally displaceable on the pillar, this truck carrying the x-ray system. In the x-ray examination apparatus of the invention, a truck carrying the x-ray system is adjustable on the pillar in longitudinal direction, whereby special rails for this truck are not required. The rails are formed by the pillar itself fashioned as a hollow profile, namely, by the walls thereof. The pillar can thereby be expediently manufactured of light metal in an extrusion molding method.

BRIEF DESCRIPTION OF THE DRAWINGS

The invention shall be set forth in greater detail below with reference to an exemplary embodiment shown in the drawing. Shown are.

DESCRIPTION OF THE PREFERRED EMBODIMENTS

Figure 1:
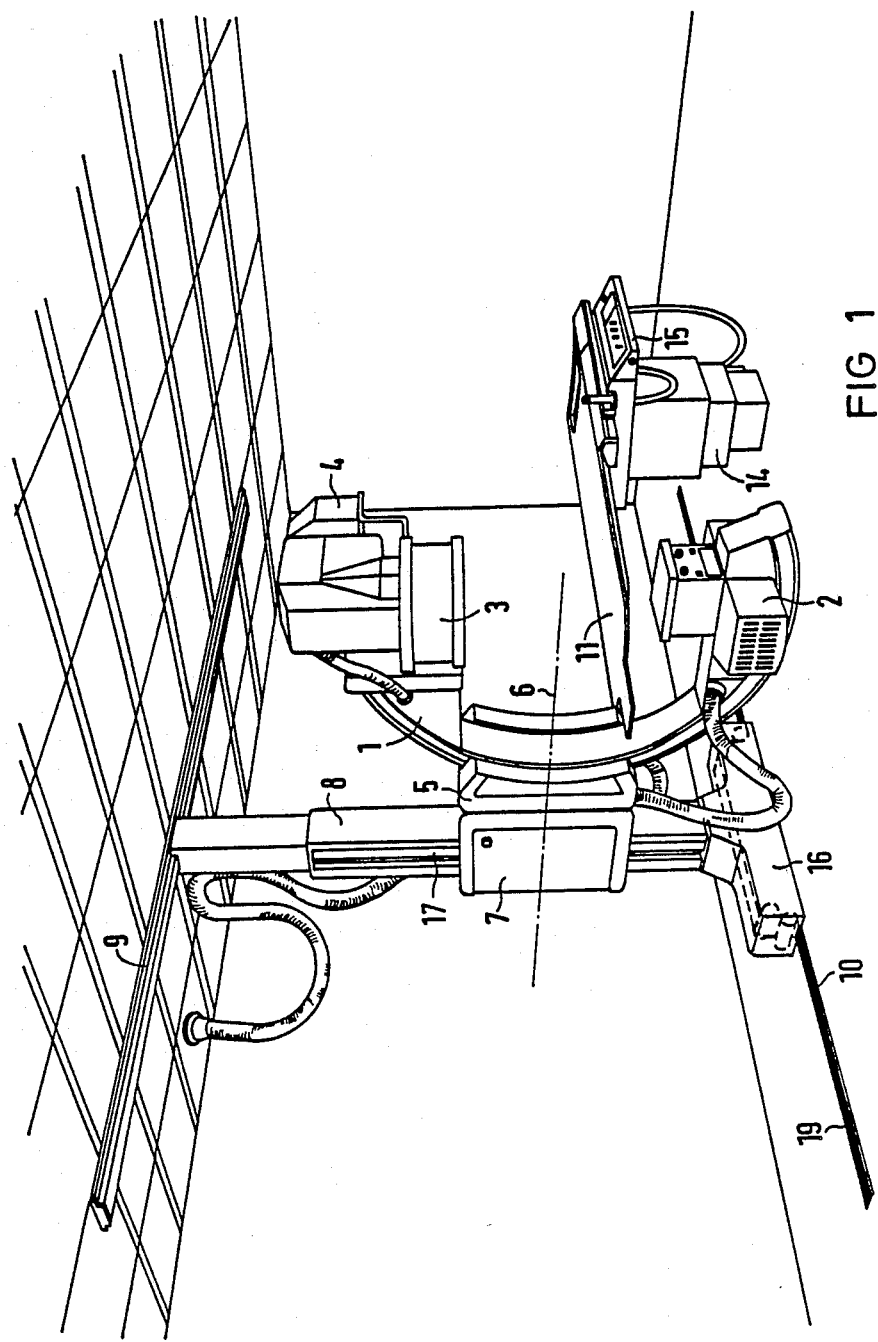
FIG. 1 is a perspective view of an x-ray examination apparatus of the invention.

FIG. 1 shows a C-bend 1 whose ends carry an x-radiator 2 and an x-ray intensifier 3 having a following single-frame camera 4 as well as a television camera (not visible). The C-bend 1 is displaceably seated along its circumference at a holder 5 which is connected to a truck 7 pivotable around a horizontal axis 6. The truck 7 is seated longitudinally displaceable at a vertical pillar 8 which is displaceable in a ceiling rail 9 and a floor rail 10 which proceed parallel to one another and to the longitudinal direction of a patient supporting table 11. This C-bend 1 transversely embraces the patient supporting table 11. The patient supporting table 11 is height-adjustably seated on a pedestal 14 to which a control panel 15 is secured. It is adjustable in longitudinal and transverse direction relative to the pedestal 14 (floating bearing), whereby, however, the regulating distance in longitudinal direction is relatively small (order of magnitude 40 cm).

The selection of the examination area essentially ensues by adjusting the x-radiator 2 and the x-ray image intensifier 3, i.e. not by adjusting the patient support table 11. The adjustment can thereby ensue in the following way:

First, the pillar 8 is moved all the way to the left under motor drive. In the position thus reached, the C-bend 1 is brought into the desired examination position (image intensifier 3 above or below the patient supporting table 11 or positioned laterally therefrom). Subsequently, the pillar 8 is brought back to such a degree until the x-radiator 2 and the x-ray image intensifier 3 lie under or, respectively, above the area of the patient to be transilluminated or lie laterally therefrom. The height of the isocenter is thereby set via vertically positioning the truck 7. Finally, the beam direction can also be additionally varied by pivoting the C-bend 1 around the axis 6.

Figure 2:
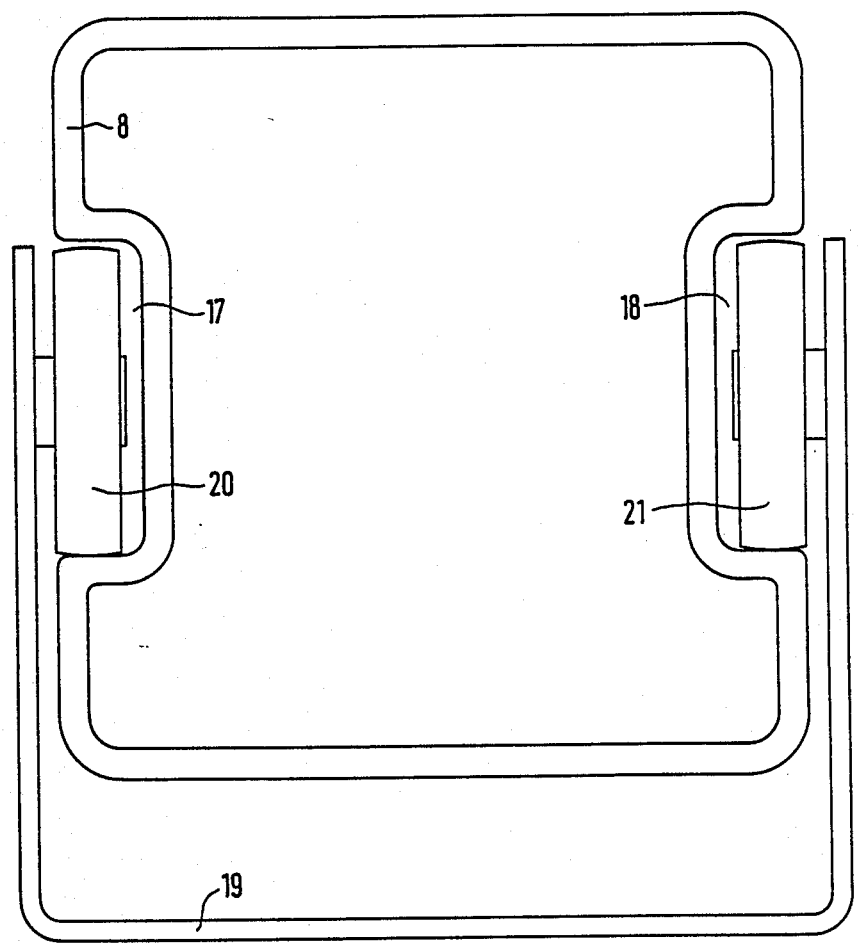
FIG. 2 is a sectional view of the pillar of the x-ray examination apparatus of FIG. 1.

FIG. 2 shows that the pillar 8 is composed of a closed box profile which includes a U-shaped depression 17, 18 proceeding in longitudinal direction at each of two parallel long sides which lie opposite one another. The depressions 17, 18 serve as rails for the truck 7. A shackle-shaped part 19 of the truck 7 is shown, wheels 20, 21 being rotatably seated thereat, these wheels rolling in the depressions 17, 18 in longitudinal direction of the pillar 8. Thus separate guide rails are not required for attachment to the pillar.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. An x-ray examination apparatus comprising a vertical pillar carrying an x-ray system, a truck which carries said x-ray system being seated in longitudinally displaceable fashion on said pillar, wherein said pillar is a hollow, one piece closed box profile and includes U-shaped depressions proceeding in longitudinal direction at each of two parallel long sides lying opposite one another, said truck comprising a U-shaped shackle with two free ends having wheels rotatably seated at said ends, said wheels rolling in said depressions in longitudinal direction of said pillar, such that said depressions serve as rails for said truck carrying said x-ray system.

2. An x-ray examination apparatus comprising:
   a vertical pillar carrying an x-ray system;
   said pillar being fabricated of a single piece of material and having a hollow closed box profile with U-shaped channels extending longitudinally in two parallel long sides of said pillar which lie opposite each other,
   a truck which carries said x-ray system, said truck comprising a U-shaped shackle with two free ends having wheels rotatably seated at said ends, said wheels being seated in longitudinally displaceable fashion in said channels on said pillar;

such that said channels act as rails for said truck.

3. An x-ray examination system according to claim 2, wherein said pillar is an extrusion molded tube.

4. An x-ray examination apparatus comprising:
 a C-bend carrying an x-radiator and an x-ray receiver at its ends;
 a holder for displaceably seating said C-bend along its circumference;
 a vertical pillar;
 a truck carrying said holder, said truck comprising a U-shaped shackle with two free ends having wheels rotatably seated at said ends, said wheels rolling in said depressions in longitudinal direction of said pillar and said holder being pivotable about a horizontal axis on said truck;
 a ceiling rail and a floor rail proceeding parallel to each other;
 said pillar being displaceably carried in said floor and ceiling rail;
 a patient support table aligned with said floor and ceiling rails and supported independently of said pillar;
 said pillar being fabricated with a hollow closed box profile with U-shaped channels extending longitudinally in two parallel long sides of said pillar which lie opposite one another, said channels acting as rails for said truck.

* * * * *